United States Patent [19]

Cooper et al.

[11] Patent Number: 5,376,663

[45] Date of Patent: Dec. 27, 1994

[54] MACROCYCLIC COMPOUNDS

[75] Inventors: Martin E. Cooper, Loughborough;
David K. Donald, Ashby de la Zouch;
David N. Hardern, Loughborough,
all of England

[73] Assignee: Fisons plc, Ipswich, United Kingdom

[21] Appl. No.: 391,538

[22] PCT Filed: Dec. 2, 1988

[86] PCT No.: PCT/GB88/01093

§ 371 Date: Jul. 25, 1989

§ 102(e) Date: Jul. 25, 1989

[87] PCT Pub. No.: WO89/05304

PCT Pub. Date: Jun. 15, 1989

[30] Foreign Application Priority Data

Dec. 9, 1987 [GB] United Kingdom ............... 8728820

[51] Int. Cl.⁵ ............... A61K 31/395; A61K 31/445; C07D 498/16
[52] U.S. Cl. ............... 514/291; 514/418; 514/183; 540/456
[58] Field of Search ............... 540/456, 457, 436; 562/899; 514/185, 291, 278, 287

[56] References Cited

U.S. PATENT DOCUMENTS

| | | | |
|---|---|---|---|
| 4,668,669 | 5/1987 | Barriere et al. | 514/183 |
| 4,894,366 | 1/1990 | Okuhara et al. | 540/456 |
| 4,981,792 | 1/1991 | Inamine et al. | 540/456 |

FOREIGN PATENT DOCUMENTS

| | | |
|---|---|---|
| 184162 | 11/1985 | European Pat. Off. |
| 227355 | 7/1987 | European Pat. Off. |

OTHER PUBLICATIONS

Morrison and Boyd, Organic Chemistry (Boston, Allyn and Bacon, 1979) pp. 556 to 558.
Williams et al JACS 1981 103 7398-7399.
Casepio, et al JACS 1958 80 2584-2585.
Chang, et al JACS 1960 82 1401-5.

Morrison and Boyd, Organic Chemistry (Allyn and Bacon, 1979, Boston) pp. 639 to 640.

*Primary Examiner*—Robert T. Bond
*Attorney, Agent, or Firm*—McAulay Fisher Nissen Goldberg & Kiel

[57] ABSTRACT

Compounds of formula (I), in which [$R^1$ and $R^2$], [$R^3$ and $R^4$] and [$R^5$ and $R^6$] represent a carbon-carbon bond or two hydrogen atoms; $R^2$ additionally represents alkyl; $R^7$, $R^8$ and $R^9$ represent groups including H or OH, $R^{10}$ has various significances including alkyl and alkenyl; X and Y represent groups including O and (H, OH); $R^{14}$, $R^{15}$, $R^{16}$, $R^{17}$, $R^{18}$, $R^{19}$, $R^{22}$ and $R^{23}$ represent H or alkyl; $R^{20}$ and $R^{21}$ represent groups including O, (H, OH) and (H, O-alkyl), n is 1, 2 or 3, and in addition, Y, $R^{10}$ and $R^{23}$, together with the carbon atoms to which they are attached, may represent a heterocyclic ring, (with certain provisos) are described. Processes for making the compounds and pharmaceutical formulations containing them, e.g. for use as immunosuppressive agents, are also described.

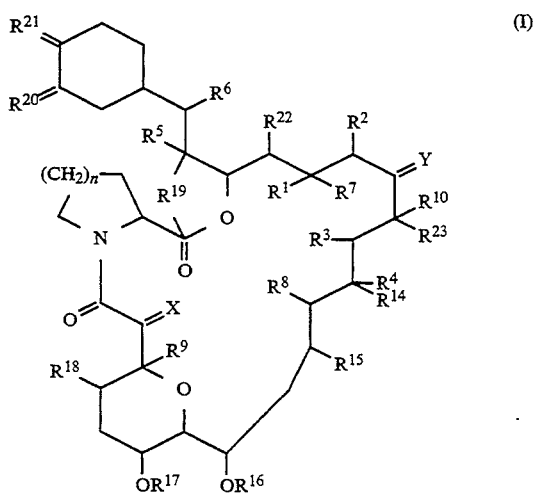

8 Claims, No Drawings

MACROCYCLIC COMPOUNDS

This invention relates to novel compounds, methods for their preparation, their use as medicaments, and compositions containing them.

European Patent Application 0184162 (to Fujisawa Pharmaceuticals Co. Ltd.) discloses a number of macrolides isolated from microorganisms belonging to the genus Streptomyces. The macrolides are numbered FR-900506, FR-900520, FR-900523 and FR-900525, and may be used as starting materials to produce the compounds of the present invention.

According to the invention, we provide compounds of formula I,

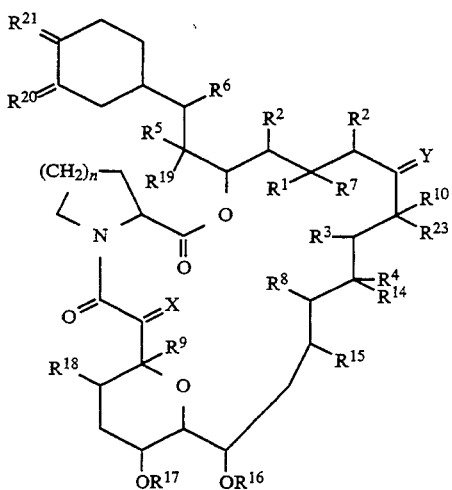

wherein each vicinal pair of substituents [$R^1$ and $R^2$], [$R^3$ and $R^4$], [$R^5$ and $R^6$] independently
a) represent two vicinal hydrogen atoms, or
b) form a second bond between the vicinal carbon atoms to which they are attached;
in addition to its significance above, $R^2$ may represent an alkyl group;

$R^7$ represents H, OH or O-alkyl, or in conjunction with $R^1$ it may represent =O, $R^8$ and $R^9$ independently represent H or OH;

$R^{10}$ represents H, alkyl, alkyl substituted by one or more hydroxyl groups, alkenyl, alkenyl substituted by one or more hydroxyl groups, or alkyl substituted by =O;

X represents O, (H,OH) (H,H) or —CH$_2$O—;

Y represents O, (H,OH), (H,H), N—NR$^{11}$R$^{12}$ or N—OR$^{13}$;

$R^{11}$ and $R^{12}$ independently represent H, alkyl, aryl or tosyl;

$R^{13}$, $R^{14}$, $R^{15}$, $R^{16}$, $R^{17}$, $R^{18}$, $R^{19}$, $R^{22}$ and $R^{23}$ independently represent H or alkyl;

$R^{20}$ and $R^{21}$ independently represent O, or they may independently represent ($R^{20}$a,H) and ($R^{21}$a,H) respectively; $R^{20}$a and $R^{21}$a independently represent OH, O-alkyl or OCH$_2$OCH$_2$CH$_2$OCH$_3$, in addition, $R^{20}$a and $R^{21}$a may together represent an oxygen atom in an epoxide ring;

n is 1, 2 or 3;

in addition to their significances above, Y, $R^{10}$ and $R^{23}$, together with the carbon atoms to which they are attached, may represent a 5- or 6-membered N-, S- or O-containing heterocyclic ring, which may be saturated or unsaturated, and which may be substituted by one or more groups selected from alkyl, hydroxyl, alkyl substituted by one or more hydroxyl groups, O-alkyl, benzyl and —CH$_2$Se(C$_6$H$_5$);

provided that when X and Y both represent O; $R^9$ represents OH; $R^{14}$, $R^{15}$, $R^{16}$, $R^{17}$, $R^{18}$, $R^{19}$ and $R^{22}$ each represent methyl; $R^{20}$a represents OCH$_3$; $R^8$ and $R^{23}$ each represent H; $R^{21}$a represents OH; [$R^3$ and $R^4$] and [$R^5$ and $R^6$] each represent a carbon-carbon bond, and
a) when n=1, $R^7$ represents an OH group and $R^1$ and $R^2$ each represent hydrogen, then $R^{10}$ does not represent an allyl group,
b) when n=2, $R^7$ represents OH and $R^1$ and $R^2$ each represent hydrogen, then $R^{10}$ does not represent methyl, ethyl, propyl or allyl, and
c) when n=2, $R^7$ represents hydrogen and [$R^1$ and $R^2$] represents a carbon-carbon bond, then $R^{10}$ does not represent an allyl group;
and pharmaceutically acceptable salts thereof.

Pharmaceutically acceptable salts of the compounds of formula I include acid addition salts of any amine groups present.

Preferably when $R^2$, $R^7$, $R^{11}$, $R^{12}$, $R^{13}$, $R^{14}$, $R^{15}$, $R^{16}$, $R^{17}$, $R^{18}$, $R^{19}$, $R^{20}$a, $R^{21}$a, $R^{22}$ and $R^{23}$ comprise carbon-containing groups, those groups contain up to 10 carbon atoms, more preferably from 1 to 6, e.g. methyl or methoxyl.

We prefer each of $R^{14}$, $R^{15}$, $R^{16}$, $R^{17}$, $R^{18}$, $R^{19}$ and $R^{22}$ to represent methyl.

Alkyl groups which $R^2$, $R^7$, $R^{10}$, $R^{11}$, $R^{12}$, $R^{13}$, $R^{14}$, $R^{15}$, $R^{16}$, $R^{17}$, $R^{18}$, $R^{19}$, $R^{20}$a, $R^{21}$a, $R^{22}$ and $R^{23}$ may comprise include straight chain, branched and cyclic groups.

Alkyl groups substituted by =O which $R^{10}$ may represent include ketone and aldehyde groups.

Preferably, $R^{10}$ is allyl (i.e. prop-2-enyl), propyl, ethyl or methyl.

Preferably, n is 2.

We prefer $R^7$ to be H or OH.

Preferably, $R^1$ and $R^2$ both represent H.

X is preferably O or (H,OH).

We prefer $R^{20}$a and $R^{21}$a to (independently) represent OH or OCH$_3$.

When Y, $R^{10}$ and $R^{23}$ together represent a N-, S- or O- containing heterocyclic ring, we prefer that ring to be five-membered, more preferably a pyrrole or tetrahydrofuran ring.

According to the invention there is further provided a process for the preparation of compounds of formula I, or pharmaceutically acceptable salts thereof. The starting material for a compound of the present invention is preferably one of the macrolides isolated from microorganisms of the genus Streptomyces, which are disclosed in European Patent Application 0184162. One or more processes discussed below may be employed to produce the desired compound of the invention.

Such a process comprises:
(a) producing a compound of formula I, in which one or more of [$R^1$ and $R^2$], [$R^3$ and $R^4$] or [$R^5$ and $R^6$] represent two vicinal hydrogen atoms, by selective reduction of a corresponding group [$R^1$ and $R^2$], [$R^3$ and $R^4$] or [$R^5$ and $R^6$] when it represents a second bond between two vicinal carbon atoms in a corresponding compound,
(b) producing a compound of formula I, which contains one or more hydroxyl groups, by selective reduction of one or more C=O groups in a corresponding compound, (c) producing a compound of formula I, which contains a

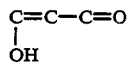

group, by selective oxidation of a

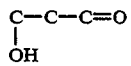

group in a corresponding compound, (d) producing a compound of formula I, which contains one or more alkoxy groups, by alkylation of one or more hydroxyl groups in a corresponding compound by reaction with a suitable alkylating agent, (e) producing a compound of formula I, which contains one or more hydroxyl groups, by deprotection of one or more protected hydroxyl groups in a corresponding compound where the protecting group is preferably removable by hydrogenolysis, (f) producing a compound of formula I, which contains a carbon-carbon double bond, by elimination of HL from a corresponding compound, where L is a leaving group, (g) producing a compound of formula I, in which Y, $R^{23}$ and $R^{10}$, together with the carbon atoms to which they are attached, form a tetrahydrofuran ring substituted by a $CH_2Se(C_6H_5)$ group, by reacting a phenylselenyl halide with a corresponding compound in which Y is O and $R^{10}$ is allyl, (h) producing a compound of formula I, which contains an allylic alcohol, by selective oxidation of an allyl group in a corresponding compound, (i) producing a compound of formula I, which contains a ketone group, by oxidation of a hydroxyl group in a corresponding compound, (j) producing a compound of formula I, which contains a vicinal diol, by oxidation of a carbon-carbon double bond in a corresponding compound, (k) producing a compound of formula I, which contains an aldehyde group, by oxidative cleavage of a vicinal diol in a corresponding compound, (l) producing a compound of formula I, in which Y, $R^{10}$ and $R^{23}$, together with the carbon atoms to which they are attached, form a pyrrole ring, by reacting ammonia or an amine with a corresponding compound in which Y is O and $R^{10}$ is —$CH_2CHO$, (m) producing a compound of formula I, which contains an epoxide group, by cyclization of an

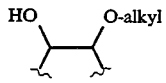

group in a corresponding compound, (n) producing a compound of formula I, in which Y represents an oxime group, by reaction of a corresponding compound in which Y is O with an oxygen-substituted amine.

(o) producing a compound of formula I, which contains a $COCH_3$ group, by oxidation of a terminal alkene group in a corresponding compound, (p) producing a compound of formula I, in which X represents —$CH_2O$—, by reacting a corresponding compound in which X is O with diazomethane, or (q) producing a compound of formula I, in which Y is a hydrazone or a hydrazone derivative, by reacting a corresponding compound in which Y is O with hydrazine or a substituted hydrazine.

In process (a), reduction may be carried out catalytically using hydrogen. Suitable catalyts include platinum catalysts (e.g. platinum black, platinum oxides), palladium catalysts (e.g. palladium oxide, palladium on charcoal), nickel catalysts (e.g. nickel oxide, Raney nickel), and rhodium catalysts (e.g. rhodium on alumina). Suitable solvents are those which do not adversely affect the reaction, and include methanol, ethanol, ethyl acetate, dichloromethane and dimethylformamide. The reduction may be carried out at or around room temperature.

Reduction may also be achieved by other means. For example, when the carbon-carbon double bond is conjugated with a ketone group, the reduction may be effected using an alkyl tin hydride, for example tri n-butyl tin hydride, in the presence of a catalyst, for example tetrakis(triphenylphosphine) palladium (0). In this case, the reaction is preferably carried out in a solvent which does noy adversely affect the reaction, for example toluene or benzene, and preferably under slightly acidic conditions, for example in the presence of a trace of acetic acid.

In process (b), suitable reagents include sodium borohydride, zinc in acetic acid, sodium triacetoxyborohydride in acetic acid, L-Selectride (Registered Trade Mark) in tetrahydrofuran, or preferably borane/$^t$butylamine complex in a solvent such as methanol or ethanol. The reduction may be conducted at or around room temperature.

In process (c), suitable oxidizing agents include dialkyl sulphoxides (e.g. dimethyl-sulphoxide, methylethylsulphoxide). The oxidation may be carried out in a solvent which does not adversely affect the reaction (e.g. acetone, dichloromethane, tetrahydrofuran) in the presence of an alkanoic anhydride. We prefer the anhydride to be acetic anhydride, as this may also function as the solvent for the reaction. The reaction may be conducted at or around room temperature.

In process (d), suitable alkylating agents include alkyl tosylates, diazoalkanes and alkyl halides (e.g. alkyl chlorides, bromides and iodides). Suitable solvents include those which are inert under the reaction conditions. We prefer polar, aprotic solvents such as dimethylformamide, 1,4-dioxan and acetonitrile. When the alkylating agent is an alkyl halide, the reaction is preferably carried out in the presence of a base, e.g. potassium carbonate, at a temperature of from about 0° to 100° C.

In process (e), when the hydroxyl protecting group is hydrogenolysable, hydrogenolysis may be carried out in a solvent which is inert to the reaction conditions, e.g. in an alcoholic solvent such as ethanol or methanol. Hydrogenolysable hydroxyl protecting groups include arylmethyl groups, in particular substituted and unsubstutited phenylmethyl groups. The reaction is preferably carried out using hydrogen at a pressure of from about 1 to 3 atmospheres using a metal catalyst on a support, e.g. palladium on charcoal. The hydrogenolysis is preferably carried out at a temperature of from about 0° to 50° C.

In process (f), L may be halogen or hydroxy for example.

When the precursor compound contains a

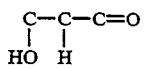

group, the elimination of H₂O may be carried out in a solvent which is inert under the reaction conditions (e.g. toluene) with a trace amount of acid (e.g. tosic acid), at a temperature from about 50° to 100° C.

In process (g), the reaction may be conducted by reacting a corresponding compound in which Y is O and $R^{10}$ is allyl, with phenylselenylbromide, using methanol as solvent, at a temperature below 0° C., preferably from −20° to −80° C.

In process (h), suitable oxidizing agents include selenium dioxide (when other oxidizable goups are either absent or protected), preferably in the presence of 'butyl hydrogen peroxide. Suitable solvents include dichloromethane, and the reaction is preferably conducted at a temperature of from 0° to 50° C., more preferably 15°–25° C.

In process (i), suitable reagents include acidified sodium dichromate and aluminium t-butoxide (the Oppenauer method). Suitable solvents include acetone in each case; but with sodium dichromate we prefer the solvent to be acetic acid; and with aluminum t-butoxide, benzene or toluene may be added as a co-solvent. Sodium dichromate is preferably used at or around room temperature, while aluminium t-butoxide is preferably used at the reflux temperature of the reaction mixture.

In process (j), suitable reagents include osmium tetroxide, potassium permanganate, and iodine in conjunction with silver acetate. Osmium tetroxide is preferably used with a regenerating agent such as hydrogen peroxide, alkaline t-butyl hydroperoxide or N-methylmorpholine-N-oxide, and a solvent which does not adversely affect the reaction, for example diethyl ether or tetrahydrofuran. Potassium permanganate is preferably used in mild conditions, for example alkaline aqueous solution or suspensions. Co-solvents such as t-butanol or acetic acid may also be used.

Iodine-silver acetate under 'wet' conditions yields cis-diols. Preferably, iodine is used in aqueous acetic acid in the presence of silver acetate. Iodine-silver acetate under 'dry' conditions yields trans-diols. Here, the initial reaction is carried out in the absence of water, and final hydrolysis yields the diol (Prevost reaction). In each case, the oxidation is preferably carried out at a temperature from 0° to 100° C., more preferably at or around room temperature.

In process (k), suitable reagents include lead tetraacetate, phenyliodoso acetate, periodic acid or sodium metaperiodate. Suitable solvents for the first two reagents include benzene and glacial acetic acid. The second two reagents are preferably used in aqueous solution. The reaction is preferably carried out at a temperature of from 0° to 100° C., more preferably at or around room temperature.

In process (1) a pyrrole ring in which the nitrogen atom is unsubstituted may be produced by reacting a corresponding compound in which Y is O and $R^{10}$ is —CH₂CHO with ammonia. Pyrrole rings in which the nitrogen atom is substituted may be produced by reacting the precursor compound with a substituted amine, for example 2-aminoethanol or benzylamine. Suitable solvents include those which do not adversely affect the reaction, for example dichloromethane. The reaction is preferably carried out at a temperature of from 0° to 100° C., more preferably at or around room temperature.

In process (m), suitable reagents include boron trifluoride followed by diazomethane. Suitable solvents are those which do not adversely affect the reaction, for example dichloromethane. The reaction is preferably carried out at a temperature of from 0° to 100° C., more preferably at or around room temperature.

In process (n), suitable oxygen-substituted amines include hydroxyl amine and O-alkyl hydroxyl-amines, for example O-methyl hydroxylamine. Suitable solvents include those which do not adversely affect the reaction, for example ethanol or methanol. The reaction is preferably carried out at a temperature of from 50°-200° C., more preferably at the reflux temperature of the solvent.

In process (o), suitable reagents include a palladium (II) halide, for example palladium (II) chloride, in conjunction with a cuprous halide, for example cuprous chloride. Suitable solvents include those that do not adversely affect the reaction, for example dimethyl formamide and water. The reaction is preferably carried out at a temperature of from 0° to 100° C., more preferably at or around room temperature.

In process (p), suitable solvents include those which do not adversely affect the reaction, for example dichloromethane. the reaction is preferably carried out at a temperature of from 0° to 50° C., more preferably at or around room temperature.

In process (q), suitable reagents include hydrazine and toluene-4-sulphonylhydrazide. Suitable solvents include those which do not adversely affect the reaction conditions, for example methanol or ethanol. The reaction is preferably carried out at a temperature of from 0° to 50° C., more preferably at or around room temperature.

D. Askin et al (Tetrahedron Letts; 1988, 29, 277), S. Mills et al (ibid; 1988, 29, 281) and D Donald et al (ibid; 1988, 29, 4481) have recently disclosed synthetic routes to fragments of macrolide FR-900506 mentioned above. Their approaches may be incorporated into a process for producing the novel compounds of the present invention, in particular when one or more of $R^{14}$, $R^{15}$, $R^{16}$, $R^{17}$, $R^{18}$, $R^{19}$ or $R^{22}$ is other than methyl.

The processes described above may produce the compound of formula I or a salt thereof. It is also within the scope of this invention to treat any salt so produced to liberate the free compound of formula I, or to convert one salt into another.

The compounds of formula I, and pharmaceutically acceptable salts thereof, are useful because they possess pharmacological activity in animals; in particular they are useful because they possess immunosuppressive activity, e.g. in the tests set out in Examples A, B and C. Thus the compounds are indicated for use in the treatment or prevention of the resistance by transplantion of organs or tissues, such as kidney, heart, lung, bone marrow, skin, etc, and of autoimmune and proliferative diseases such as rheumatoid arthritis, systemic lupus erythematosus, Hashimoto's thyroiditis, multiple sclerosis, myasthenia gravis, type 1 diabetes, uveitis, psoriasis, etc. Some of the compounds of the invention are also indicated for use as antimicrobial agents, and thus may be used in the treatment of diseases caused by pathogenic microorganisms and the like.

We therefore provide the use of compounds of formula I (and pharmaceutically acceptable salts thereof) as pharmaceuticals.

Further, we provide the use of a compound of formula I (and pharmaceutically acceptable salts thereof) in the manufacture of a medicament for use as an immunosuppressive agent.

For the above-mentioned therapeutic uses the dosage administered will, of course, vary with the compound employed, the mode of administration, the treatment desired (e.g. topical, parenteral or oral) and the disease indicated. However, in general, satisfactory results are obtained when the compounds are administered at a dosage of from 0.1 to 200 mg per kg of animal body weight. For man the indicated total daily dosage is in the range of from 1 mg to 1000 mg and preferably from 10 mg to 500 mg, which may be administered, for example twice weekly, or in divided doses from 1 to 6 times a day or in sustained release form. Thus unit dosage forms suitable for administration, e.g. oesophageally, comprise from 2 mg to 500 mg, and preferably 1 mg to 500 mg of the compound preferably admixed with a solid or liquid pharmaceutically acceptable diluent, carrier or adjuvant.

According to our invention we also provide a pharmaceutical composition comprising (preferably less than 80%, and more preferably less than 50% by weight) of a compound of formula I, or a pharmaceutically acceptable salt thereof, in combination with a pharmaceutically acceptable adjuvant, diluent or carrier. Examples of suitable adjuvants, diluents or carriers are: for tablets, capsules and dragees; microcrystalline cellulose, calcium phosphate, diatomaceous earth, a sugar such as lactose, dextrose or mannitol, talc, stearic acid, starch, sodium bicarbonate and/or gelatin; for suppositories, natural or hardened oils or waxes; and for inhalation compositions, coarse lactose. The compound of formula I, or the pharmaceutically acceptable salt thereof, preferably is in a form having a mass median diameter of from 0.01 to 10 microns. The compositions may also contain suitable preserving, stabilising and wetting agents, solubilisers, sweetening and colouring agents and flavourings. The compositions may, if desired, be formulated in sustained release form. We prefer compositions which are designed to be taken oesophageally and to release their contents in the gastrointestinal tract.

The compounds of formula I, and pharmaceutically acceptable salts thereof, have the advantage that they are less toxic, more efficacious, are longer acting, have a broader range of activity, are more potent, produce fewer side effects, are more easily absorbed or have other useful pharmacological properties, than compounds previously used in the therapeutic fields mentioned above.

The compounds of formula I have a number of chiral centres and may exist in a variety of stereoisomers. The invention provides all optical and stereoisomers, as well as racemic mixtures. The isomers may be resolved or separated by conventional techniques.

EXAMPLE A

Mixed Lymphocyte Reaction (MLR) I

The MLR test was performed in microtitre plates, with each well containing $5 \times 10^5$ C57BL/6 responder cells (H-$2^b$), $5 \times 10^5$ mitomycin C treated (25 ug/ml mitomycin C at 37° C. for 30 minutes and washed three times with RPMI 1640 medium) BALB/C stimulator cells (H-$2^d$) in 0.2 ml RPMI 1640 medium supplemented with 10% fetal calf serum, 2 mM sodium hydrogen carbonate, penicillin (50 unit/ml) and streptomycin (50 ug/ml). The cells were incubated at 37° C. in a humidified atmosphere of 5% carbon dioxide and 95% of air for 68 hours and pulsed with $^3$H-thymidine (0.5 uCi) 4 hours before the cells were collected. The object compound of this invention was dissolved in ethanol and further diluted in RPMI 1640 medium and added to the cultures to give final concentrations of 0.1 ug/ml or less.

EXAMPLE B

Mixed Lymphoctye Reaction (MLR) II

The MLR test was performed in 96-well microtitre plates with each well containing $3 \times 10^5$ cells from each of two responding donors in a final volume of 0.2 ml RPMI 1640 medium supplemented with 10% human serum, L-glutamine and penicillin/streptomycin. The compound under test was dissolved at 10 mg/ml in ethanol and further diluted in RPMI 1640. The cells were incubated at 37° C. in a humidified atmosphere of 5% carbon dioxide for 96 hours. $^3$H-thymidine (0.5 uCi) was added for the final 24 hours of the incubation to provide a measure of proliferation.

EXAMPLE C

Graft versus Host Assay (GVH)

Spleen cells from DA and DAxLewis F1 hybrid rats were prepared at approximately $10^8$ cells/ml. 0.1 ml of these suspensions were injected into the rear footpads of DAxLewis F1 rats (left and right respectively). Recipient animals were dosed with the compound under test, either orally or subcutaneously, on days 0–4. The assay is terminated on day 7 when the popliteal lymph nodes of the animals were removed and weighed. The increase in weight of the left node relative to the weight of the right is a measure of the GVH response.

The invention is illustrated by the following Examples.

EXAMPLE 1

17-Allyl-1-hydroxy-12-[2-(3,4-dimethoxycyclohexyl)-1-methylvinyl]-14,23,25-trimethoxy-13,19,21,27-tetramethyl-11,28-dioxa-4-azatricyclo[22.3.1.0$^{4,9}$]octacos-18-ene-2,3,10,16-tetraone To a stirred solution of the macrolide FR 900506 (200 mg) in dichloromethane (30 ml) and ether (20 ml) was added boron trifluoride diethyl ether complex (10 mg) and then a solution of diazomethane (600 mg) in ether (30 ml) added slowly over 5 minutes with evolution of nitrogen. The products were purified by chromatography on silica, with ether as the eluant, to yield the title compound (55 mg), characterised by nmr and mass spectroscopy.

MS: (FAB) 831 (molecular ion)

$^{13}$C NMR δ: 210.0 (C16); 196.52(C2); 166.9 (C10); 164.6 (C3); 138.5 (C19); 135.6 (C41); 133.9 (C29); 131.5 (C31); 123.3 (C18); 116.5 (C42); 97.6 (C1); 83.1 (C34); 82.6 (C35); 79.0 (C14)

EXAMPLE 2

17-Allyl-1,14-dihydroxy-12-[2-(3,4-dimethoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of macrolide FR 900506 (80 mg) in dichloromethane (100 ml) and ether (50 ml) was added 35–70 micron silica (5 g) and then diazomethane (300 mg) in ether (50 ml) was added slowly over 5 minutes with evolution of nitrogen. After stirring for a further 15 minutes the products were purified by chromatography on silica, with ether as eluant, to yield the title compound (15 mg), characterised by nmr and mass spectroscopy.

MS: (FAB) 840.8 (MI+Na)

$^{13}$C NMR δ: 212.8 (C16); 196.2 (C2); 169.0 (C.10); 164.7 (C3); 139.0 (C19); 135.6 (C41); 132.4 (C29); 129.7 (C31); 122.4 (C18); 116.7 (C42); 97.0 (C1); 83.2 (C34); 82.6 (C35)

EXAMPLE 3

1,14-Dihydroxy-12-[2-(4-hydroxy-3-methoxycyclohexyl)-1-methylvinyl]-18-[(phenylseleno)methyl]-16,26,28-trimethoxy-13,22,24,30-tetramethyl-11,17,31-trioxa-4-azatetracyclo[25.3.1.0$^{16,20}$]hentriacont-21-ene-2,3,10-trione To a solution of the macrolide FR 900506 (62 mg, 7.7×10$^{-5}$ moles) in dry methanol (12 ml) at −78° C. under nitrogen was added 2,6-dimethylpyridine (9.9 mg, 9.24×10$^{-5}$ moles). To this was then added a solution of 0.46 mg of phenylselenylbromide in acetonitrile (0.47 ml of a solution of 0.46 mg of phenylselenylbromide in 1 ml of acetonitrile), followed after 20 minutes by 0.53 ml of the same solution. The reaction mixture was then evaporated at low temperature in vacuo and the residue was chromatographed on silica eluting with dichloromethane/ethyl acetate (2:1) to give the product as a mixture of diastereoisomers (65.5 mg) which could be further separated by HPLC.

MS: (FAB) 1013 (MI+Na).

$^{13}$C NMR δ: 133.2, 129.2, 127.4 (Ar); 111.6 (C10); 97.5 (C1); 78.0 (C14); 76.7 (C41); 55.8 (C9); 50.3, 49.5 (C10 rotamers); 49.8 (C17); 41.2 (C15); 31.2 (C42); 29.7 (C40).

EXAMPLE 4

17-Allyl-1-hydroxy-12-[2-(3,4-dimethoxycyclohexyl)-1-methylvinyl]-23,25-dimethoxy-13,19,21,27-tetramethyl-11,28-dioxa-4-azatricyclo[22.3.1.0$^{4,9}$]octacosa-14,18-diene-2,3,10,16-tetraone A stirred solution of 17-Allyl-1,14-dihydroxy-12-[2-(3,4-dimethoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (10 mg, prepared by methylation of macrolide FR 900506), in toluene (5 ml) containing a trace of tosic acid was heated on a steam bath for 5 minutes. Removal of solvent in vacuo and chromatography on silica eluting with ethyl acetate gave the title compound as an oil (8 mg).

MS: (FAB) 822.8 (MI+Na) 800.9 (MI+H)

$^{13}$C NMR δ: 200.4 (C16); 192.2 (C2); 169.2 (C10); 165.0 (C3); 148.2 (C14); 138.3 (C39); 135.4 (C41); 131.4, 130.0, 127.6 (C15, C29, C31); 124.1 (C18); 116.5 (C42); 97.9 (C1); 83.3 (C34); 83.0 (C35); 79.8 (C12).

EXAMPLE 5

17-Allyl-1,2,14-trihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-3,10,16-trione To a solution of the macrolide FR 900506 (100 mg) in methanol (5 ml) was added a solution of Borane 'Butylamine complex (3.7 mg) in methanol (1 ml) and the solution was stirred for 12 hours at room temperature. The solution was evaporated and chromatographed on silica using ethyl acetate as eluent to give the title compound (32 mg) as a mixture of diastereoisomers.

MS: (FAB) 829 (MI+Na)

$^{13}$C NMR (showing a mixture of rotamers) δ: 212.0, 213.4 (C16); 171, 172.8 (C10); 170.4, 169.8 (C3); 140, 140.5 (C19); 135.5, 135.6 (C41); 132.4, 132.6 (C29); 129, 130 (C31); 122.5 (C18); 116.5 (C42); 99.2, 97.5 (C1).

EXAMPLE 6

17-Allyl-1,2,14,16-tetrahydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-3,10-dione To a solution of the macrolide FR 900506 (40 mg) in diethyl ether (5 ml) was added excess borane ammonia complex (100 mg) and the solution was stirred at room temperature for 1 hour. Dilute hydrochloric acid was added and the organic phase was separated and chromatographed on silica using ethyl acetate as eluent to give the title compound (25 mg) as a white solid.

MS: (FAB) 830.8 (MI+Na)

$^{13}$C NMR δ: 174.3 (C10); 171.7 (C3): 116.1 (C42). Mp 130°–150° C.

EXAMPLE 7

17-Propyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacosane-2,3,10,16-tetraone To a solution of the macrolide FR 900506 (100 mg) in methanol was added Pd-on-carbon (20 mg) and the mixture was stirred in an atmosphere of hydrogen for 20 hours. Filtration of the reaction mixture, evaporation of the solvent in vacuo and HPLC of the resulting mixture on silica gave the title product (35 mg).

EXAMPLE 8

17-Propyl-1,14-dihydroxy-12-[2-(4-hydroxy-3-methoxycyclohexyl)-1-methylethyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of the macrolide FR 900506 (100 mg) in methanol was added Pd on Carbon (20 mg) and the mixture was stirred in an atmosphere of hydrogen for 20 hours. Filtration of the reaction mixture, evaporation of the solvent in vacuo and HPLC of the resulting mixture on silica gave the title product (30 mg).

EXAMPLE 9

17-Propyl-1,14-dihydroxy-12-[2-(4-hydroxy-3-methoxycyclohexyl)-1-methylethyl]-23,25-dimethoxy-13,19,21,27-tetramethyl-11,28-dioxa-4-azatricyclo[22.3.1.0$^{4,9}$]octacosane-2,3,10,16-tetraone To a solution of the macrolide FR 900506 (100 mg) in methanol was added Pd on Carbon (20 mg) and the mixture was stirred in an atmosphere of hydrogen for 20 hours. Filtration of the reaction mixture, evaporation of the solvent in vacuo and HPLC of the resulting mixture on silica gave the title product (15 mg).

EXAMPLE 10

17-Propyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of the macrolide FR 900506 (800 mg) in ethanol (20 ml) was added Pd-on-carbon (10 mg) and the mixture was stirred in an atmosphere of hydrogen for 30 minutes. Filtration of the reaction mixture, evaporation of the solvent in vacuo and chromatography on silica eluting with ether/methanol (20:1) yielded the title compound as an oil (750 mg).

$^{13}$C NMR δ: 33.32 (C40); 20.43 (C41); 14.11 (C42)

EXAMPLE 11

17-Propyl-1-hydroxy-12-[2-(4-hydroxy-3-methoxycyclohexyl)-1-methylvinyl-23,25-dimethoxy-13,19,21,27-tetramethyl-11,28-dioxa-4-azatricyclo[22.3.1.0$^{4,9}$]octacosa-14,18-diene-2,3,10,16-tetraone A stirred solution of 17-propyl-1,14-dihydroxy-1-2-[2-(4-hydroxy-3-methoxycyclohexyl)-1-methylvinyl-23,25-dimethoxy-13,19,21,27-tetramethyl-11,28-dioxa-4-azatricyclo[22.3.1.0$^{4,9}$]octacos-18-ene-2,3,10,16-tetraone (800 mg prepared by the method of example 10), in toluene (20 ml) containing 50 mg of tosic acid was heated on a steam bath for 30 minutes. Removal of solvent in vacuo and chromatography on silica eluting with ether gave the title compound as an oil (600 mg).

MS: (FAB) 811 (molecular ion+Na)

$^{13}$C NMR δ: 34.64 (C40); 20.54 (C41); 14.08 (C42); 201.21 (major), 199.76 (minor) (C16); 147.93 (major), 146.25 (minor).

EXAMPLE 12

17-Propyl-1-hydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone 0.75 ml of tributyl tin hydride, 0.06 ml of water and 150 mg of (Ph$_3$P)$_4$Pd were added in three portions over a period of 1 hour to a stirred solution of the title compound of example 11 (600 mg) in tetrahydrofuran (20 ml) at room temperature. Water was then added, and the mixture extracted into ether. Removal of solvent in vacuo and chromatography on silica eluting with ether gave the title compound as an oil (400 mg).

MS: (FAB) 813 (MI+Na)

$^{13}$C NMR δ: 212.3 (C16); 196.4 (C2); 169.4 (C10); 165.1 (C3); 138.1 (C19); 131.7 (C31); 124.3 (C18); 97.4 (C1); 84.1 (C34); 82.4 (C12).

EXAMPLE 13

17-Allyl-1,14,20-trihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 17-(1-Hydroxyprop-2-enyl)-1,14,20-trihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of the macrolide FR 900506 (140 mg) in dichloromethane (17.5 ml) at room temperature was added SeO$_2$ (700 mg), followed by tertiary-butyl hydrogen peroxide (1.05 ml of a 70% aqueous solution). The reaction mixture was left to stir for 60 hours, after which it was extracted with ethyl acetate. The organic phase was washed with water followed by brine, dried (MgSO$_4$) and concentrated in vacuo. Flash chromatography on silica eluting with ether/methanol (20:1) yielded the title compounds separately as oils (19 mg and 15 mg respectively).

$^{13}$C NMR[CDCl$_3$] δ: (first compound) 141.4(C19); 123.5(C18); 135.4(C41); 117.0(C42); 131.6(C29); 129.1(C13); 211.4(C16); 195.4(C2); 170.4(C10); 166.7(C3); 98.2(C1) and 84.1(C34)ppm, (second compound) 142.3(C19); 120.7(C18); 137.5(C41); 115.9(C42); 132.3(C29); 129.0(C31); 210.7(C16); 195.8(C2); 170.5(C10); 167.2(C3); 98.2(C1) and 84.1(C34) ppm MS: (FAB) (first compound) 904 (MI+Rb), 842 (MI+Na); (second compound) 920 (MI+Rb), 859 (MI+Na);

EXAMPLE 14

17-Allyl-1-hydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacosa-14,18-diene-2,3,10,16-tetraone A stirred solution of the macrolide FR 900506 (200 mg) in dry toluene (10 ml) containing 5 mg of tosic acid was heated on a steam bath for 30 minutes. Removal of solvent in vacuo and chromatography on silica eluting with ether gave the title compound as an oil (160 mg).

MS: (FAB) 808 (MI+Na); 786 (MI+H).

$^{13}$C NMR δ: 200.4 (C16); 196.0 (C2); 169.3 (C10); 165.0 (C3); 148.0 (C14); 138.3 (C39); 135.5 (C41); 123.4 (C18); 116.6 (C42); 98.0 (C1); 84.2 (C34); 79.8 (C12).

EXAMPLE 15

17-Allyl-1,2-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-3,10,16-trione To a stirred solution of the title compound of example 14 (60 mg) in glacial acetic acid (5 ml) was added powdered zinc (1 g). Stirring was continued for 1 hour when the reaction was complete. The reaction mixture was then extracted with ethyl acetate, washed with saturated NaHCO$_3$ solution followed by brine, dried (MgSO$_4$) and concentrated in vacuo. Chromatography on silica eluting with ether/methanol (15:1 then 10:1) gave the title compound as an oil (30 mg).

$^{13}$C NMR[CDCl$_3$] δ: 99.1(C1); 67.9(C2); 171.2 and 171.7(C10 and C3); 44.6(C5); 83.32(C12); 84.0(C34); 76.6(C23); 71.7(C24); 73.3 and 73.9(C25 and C35); 52.9(C9); 52.7(C17) and 49.5(C20) ppm.

MS: (FAB) 874 (MI+Rb); 813 (MI+Na).

EXAMPLE 16

17-Allyl-1,16-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacosa-14,18-diene-2,3,10-trione The title compound from example 14 (50 mg) was dissolved in tetrahydrofuran (3 ml) and t-butanol (0.05 ml). The resulting solution was added dropwise to a stirred solution of L-Selectride (Registered Trade Mark) (0.3 ml of a 1M solution in tetrahydrofuran) under a nitrogen atmosphere at −78° C. Stirring was continued for 40 minutes, after which saturated ammonium chloride solution (5 ml) was added and the mixture extracted with ethyl acetate. After filtration of the organic phase, and removal of solvent in vacuo, chromatography on silica eluting with ether/methanol (15:1) yielded the title compound as an oil (10 mg).

$^{13}$C NMR[CDCl$_3$] δ: 197.0(C2); 169.1(C10); 165.3(C3); 96.4(C1) and 84.2(C34) ppm.

MS: (FAB) 872 (MI+Rb); 810 (MI+Na).

EXAMPLE 17

17-Allyl-1-hydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-Allyl-1-hydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-14,18-diene-2,3,10,16-tetraone (as prepared in Example 14) (100 mg) in toluene (5 ml) and acetic acid (0.01 ml) was added tetrakis(triphenylphosphine) palladium(0) (0.01 g). After 5 minutes tri n-butyltin hydride (0.04 g) was added and the reaction mixture was stirred at room temperature for 2 hours. Water was added and the reaction mixture was extracted with ether. The ether extracts were dried (magnesium sulphate), filtered and evaporated to an oil in vacuo. Chromatography on silica eluting with ether gave the title compound as a low melting solid (70 mg).

MS: (FAB) 810.7 (MI+Na), 788.7 (MI+H).

$^{13}$C NMR δ: 211.3 (C16); 196.3 (C2); 169.2 (C10); 164.9 (C3); 138.4 (C19); 135.5 (C41); 131.6 (C29); 130.9 (C31); 123.3 (C18); 116.3 (C42); 97.2 (C1); 84.0 (C34); 82.2 (C12).

EXAMPLE 18

17-Propyl-1-hydroxy-12-[2-(3-methoxy-4-oxocyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of the title compound from Example 12 (25 mg) in acetic acid (5 ml) was added potassium dichromate (25 mg), and stirring was continued overnight. The solution was then evaporated to dryness. Chromatography on silica using ether as eluant gave the title compound (15 mg).

MS: (FAB) 810 (MI+Na); 788 (MI+H).

$^{13}$C NMR δ: 212.2 (C35); 208.7 (C16); 196.3 (C2); 169.4 (C10; 165.2 (C3); 138.2 (C19); 132.5 (C29) 129.2–124.2 (C31–C42); 97.3 (C1); 83.0 (C34); 82.0 (C12)

EXAMPLE 19

17-(2,3-Dihydroxypropyl)-1,14-dihydroxy-12-[2-(4-hydroxy-3-methoxycyclohexyl)-1-methylvinyl]-23,25-dimethoxy-13,19,21,27,-tetramethyl-11,28-dioxa-4-azatricyclo[22.3.1.0$^{4,9}$]octacos-18-ene-2,3,10,16-tetraone A solution of macrolide 900506 (70 mg), N-methylmorpholine-N-oxide (NMO) (70 mg), osmium tetroxide (4 mg) and water (0.1 ml) in tetrahydrofuran (5 ml) was stirred at room temperature for 2 hours, and then treated with powdered sodium metabisulphite (100 mg) and Florisil (Registered Trade Mark). The mixture was diluted with ethyl acetate, filtered through celite, then washed with saturated NaHCO$_3$ solution, followed by brine. The solution was dried (MgSO$_4$) and concentrated in vacuo to yield the crude title compound.

MS: (FAB) 921 (MI+Rb), 861 (MI+Na).

EXAMPLE 20

17-Ethanalyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16,-tetraone The crude title compound from Example 19 was dissolved in benzene (5 ml) and treated with lead tetraacetate (100 mg) for 2–3 minutes at room temperature. The solution was then diluted with ethyl acetate, washed with saturated NaHCO$_3$ solution followed by brine, dried (MgSO$_4$) and concentrated in vacuo to yield the crude product.

MS: (FAB) 889 (MI+Rb), 829 (MI+Na)

EXAMPLE 21

1,14-dihydroxy-12-[2-(4-hydroxy-3-methoxycyclohexyl)-1-methylvinyl]-26,28-dimethoxy-13,22,24,30-tetramethyl-11,31-dioxa-4,17-diazatetracyclo[25.3.1.0$^{4,9}$.0$^{16,20}$]hentriaconta-16(20),18,21-triene-2,3,10-trione The crude title compound from Example 20 was dissolved in dichloromethane and treated with 0.88M NH$_3$ (aq) (0.2 ml). After stirring for 5 minutes at room temperature the solution was diluted with ethyl acetate, washed with saturated NaHCO$_3$ solution, dried (MgSO$_4$) and concentrated in vacuo. Chromatography on silica yielded the title compound (18 mg).

MS: (FAB) 872 (MI+Rb), 787 (MI).

$^{13}$C NMR δ: 196.44 (C2); 169.67 (C10); 165.44 (C3); 97.53 (C1).

EXAMPLE 22

1,14-Dihydroxy-12-[2-(4-hydroxy-3-methoxycyclohexyl)-1-methylvinyl]-26,28-dimethoxy-17-(2-hydroxyethyl)-13,22,24,30-tetramethyl-11,31-dioxa-4,17-diazatetracyclo[25.3.1.0.$^{4,9}$.0$^{16,20}$]hentriaconta-16(20),18,21-triene-2,3,10-trione Following the method of Example 21, the title compound (25 mg) was prepared by treating the title compound of Example 20 with 2-aminoethanol (0.2 ml).

MS: (FAB) 915 (MI+Rb), 831 (M+H).

$^{13}$C NMR δ: 196.50 (C2); 169.32 (C10); 165.50 (C3); 97.15 (C1).

EXAMPLE 23

1,14-Dihydroxy-12-[2-(4-hydroxy-3-methoxycyclohexyl)-1-methylvinyl]-26,28-dimethoxy-13,22,24,30-tetramethyl-17-phenylmethyl-11,31-dioxa-4,17-diazatetracyclo[25.3.1.0$^{4,9}$.0$^{16,20}$]hentriaconta-16(20),18,21-triene-2,3,10-trione Following the method of Example 21, the title compound (30 mg) was prepared by treating the title compound of Example 20 with benzylamine (0.1 ml).

MS: (FAB) 960 (MI+Rb), 876 (MI).

$^{13}$C NMR δ: 196.44 (C2); 169.67 (C10); 165.44 (C3); 97.53 (C1).

EXAMPLE 24

17-Allyl-1-hydroxy-12-[2-(3,4-epoxycyclohexyl)-1-methylvinyl]-23,25-dimethoxy-13,19,21,27-tetramethyl-11,28-dioxa-4-azatricyclo[22.3.1.0$^{4,9}$]octacosa-14,18-diene-2,3,10,16-tetraone To a solution of the title compound of Example 14 (823 mg, 1.05 mmole) in dry dichloromethane (50 ml) was added boron trifluoride diethyl etherate (1 drop) followed by portionwise addition of a dried solution of diazomethane in diethyl ether until no starting material remained. Sodium carbonate was then added, and the resulting mixture stirred for 30 minutes at room temperature. The reaction mixture was then filtered, concentrated in vacuo, and chromatographed on silica eluting with 40°-60° petroleum ether/ethyl acetate [3:1] to give the title compound as an oil (45 mg).

$^{13}$C NMR δ: 51.3 (C34/C35)

MS: (FAB) 838.64 (MI+Rb), 776.85 (MI+Na).

EXAMPLE 25

17-Allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone C16 oxime A mixture of macrolide 900506 (40 mg), hydroxylamine hydrochloride (40 mg) and pyridine (20 mg) in ethanol (5 ml) was heated under reflux for 3 hours. The solution was poured into dilute hydrochloric acid and extracted into dichloromethane. The organic phase was separated and chromatographed on silica, eluting with ethyl acetate to yield the title compound as a colourless solid (25 mg).

A 1:1 mixture of syn and anti oximes was present.

$^{13}$C NMR δ: 196.8 (C2); 169.0 (C10); 165.2 (C3); 162.0 (C16); 138.7 (C19); 135.9 (C41); 132.3 (C29); 129.0 (C31); 125.2 (C18); 116.0 (C42); 97.6 (C1); 84.3 (C34).

MS: (FAB) 834 (MI).

EXAMPLE 26

17-Allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone C16 oxime O-methyl ether A mixture of macrolide 900506 (100 mg), 0-methyl hydroxylamine hydrochloride (40 mg) and pyridine (50 mg) in ethanol (5 ml) was heated under reflux for 3 hours. The solvent was evaporated and the product chromatographed on silica eluting with ethyl acetate to give the product as a colourless solid (50 mg).

A 1:1 mixture of syn and anti oximes was present.

$^{13}$C NMR δ: 196.4 (C2); 169.1 (C10); 165.2 (C3); 160.1 (C16); 138.2 (C19); 135.8 (C41); 132.6 (C29); 128 (C31); 125 (C18); 116.2 (C42); 97.0 (C1); 84.2 (C34); 61.7 (=NOCH$_3$); 56.2 (C17).

MS: (FAB) 833 (MI+H)

EXAMPLE 27

17-Allyl-1,14-dihydroxy-12-[2-(4-(2′,5′-dioxahexyloxy)-3-methoxycyclohexyl-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of macrolide 900506 (100 mg) in dichloromethane (2 ml) was added 2-methoxyethoxymethyl (MEM) chloride (155 mg) and N,N-diisopropylethylamine (160 mg). After stirring for 90 minutes at room temperature, volatiles were removed in vacuo and the reaction mixture was purified by chromatography on silica eluting with 40°-60° petroleum ether/acetone [3:1] to give the title compound as an oil (72 mg).

MS: (FAB) 915 (MI+Na)

$^{13}$C NMR δ: 95 (C1′MEM); 71.7 and 66.7 (C3′ and C4′ MEM); 58.97 (C6′MEM); 30.7 (C36); 79.4 (C35); 82.6 (C34).

EXAMPLE 28

17-Propyl-1-hydroxy-12-[2-(3,4-dihydroxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-Allyl-1,14-dihydroxy-12-[2-(3,4-dihydroxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg) in toluene (20 ml) was added p-toluenesulphonic acid (5 mg) and the resulting solution was warmed for 90 minutes on a steam bath. Evaporation of volatiles in vacuo and chromatography of the residue on silica eluting with ethyl acetate gave an oil which was dissolved in methanol (5 ml). To this was then added 10% palladium-on-carbon (20 mg) and the mixture was stirred in an atmosphere of hydrogen for 1 hour at room temperature. The reaction mixture was then filtered through celite, concentrated in vacuo and purified by chromatography on silica eluting with ethyl acetate to give the title compound as an oil (40 mg).

MS: (FAB) 799 (M+Na) 861 (M+Rb)

EXAMPLE 29

1,14-Dihydroxy-12-[2-(4-hydroxy-3-methoxycyclohexyl)-1-methylvinyl]-23,25-dimethoxy-13,19,21,27-tetramethyl-17-(2-oxopropyl)-11,28,-dioxa-4-azatricyclo[22.3.1.0$^{4,9}$]-octacos-18-ene-2,3,10,16-tetraone A solution of macrolide 900506 (250 mg) in dimethylformamide (2 ml) was added to a stirred mixture of cuprous chloride (150 mg) and palladium (2) chloride (50 mg) in dimethylformamide (6 ml) and water (1.2 ml) at room temperature. A slow stream of air was passed through the reaction mixture which was stirred at room temperature for 1.5 hours. The reaction mixture was then diluted with diethyl ether (200 ml), washed with dilute aqueous hydrochloric acid (1M×2) and brine, dried (magnesium sulphate), filtered and concentrated to an oil in vacuo. Chromatography on silica eluting with hexane/acetone [2:1] gave the title compound as a foam (158 mg).

MS (FAB) 821 (MI+H), 843 (MI+Na), 905 (MI+Rb).

$^{13}$C NMR δ: (major isomer) 97.11 (C1); 196.02 (C2); 164.60 (C.3); 168.74 (C10); 213.04 (C16); 120.83 (C18); 138.51 (C19); 132.71 (C29); 129.07 (C31); 29.64 (C42); 207.74 (C41).

(minor isomer) 98.29 (C1); 193.33 (C2); 165.75 (C3); 168.67 (C10); 212.90 (C16); 120.47 (C18); 140.29 (C19); 132.17 (C29); 129.29 (C31); 207.86 (C41).

EXAMPLE 30

17-Allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-aza-spiro[tricyclo[22.3.1.0.$^{4,9}$]octacos-18-ene-2,2′-oxirane]-3,10,16-trione A solution of diazomethane (excess) in dry ether was added to a solution of macrolide 900506 (50 mg) in dichloromethane (5 ml). The solution was stirred for 2 hours, then chromatographed on silica using ethyl acetate as eluant. The title compound was obtained as a colourless solid.

MS: (FAB) 818 (MI).

$^{13}$C NMR δ: 212 (C16); 170.4 (C10); 165.7 (C3); 139.0 (C19); 135.4 (C41); 132.4 (C29); 129.4 (C31); 132.0 (C18); 116.8 (C42); 96.7 (C1); 84.2 (C34); 61.6 (C2) 50.7 (C2a)

EXAMPLE 31

17-Ethanalyl-1,2,14-trihydroxy-12-[2-(4-hydroxy-3-methoxycyclohexyl-1-methylvinyl]-23,25-dimethoxy-13,19,21,27-tetramethyl-11,28-dioxa-4-azatricyclo[22.3.1.0$^{4,9}$]octacos-18-ene-3,10,16-trione A sample of the crude product from Example 20 (15 mg) was dissolved in acetic acid (3 ml).

Zinc dust (0.5 g) was then added and the mixture was stirred at room temperature for 30 minutes. After aqueous work up and column chromatography on silica the title compound was isolated as an oil (10 mg).

$^{13}$C NMR δ: (1:1 mixture of rotamers) 99.08, 97.75 (C1); 212.81, 209.84 (C16); 200.61, 200.27 (C41); 172.40, 171.25, 170.41, 169.84 (C10, C3); 141.28, 140.96 (C29); 133.06, 132.50 (C29); 130.32, 128.69 (C31); 121.07, 120.47 (C18).

MS: (FAB) 892 (MI+Rb), 831 (MI+Na).

EXAMPLE 32

1,14-Dihydroxy-12-[2-(4-hydroxy-3-methoxycyclohexyl)-1-methylvinyl]-26,28-dimethoxy-18-[(phenylseleno)methyl]-13,22,24,30-tetramethyl-11,17,31-trioxa-4-azatetracyclo[25.3.1.0.$^{4,9}$0.$^{16,20}$]hentriaconta-16(20),21-diene-2,3,10-trione To a cold (−78° C.) solution of macrolide 900506 (198.5 mg) and 2,6-dimethylpyridine (29 mg) in dry methanol (8 ml) was added a solution of phenylselenyl bromide (127.3 mg) in dry acetonitrile (2.2 ml) under nitrogen. Solvents were then removed in vacuo at low temperature and the residual oil was purified by column chromatography on silica eluting with dichloromethane/ethyl acetate [2:1] to yield the title compound as an oil (37 mg).

MS: (FAB) 959 (MI+H)

$^{13}$C NMR δ: 29.72 (C19); 75.76 (C18); 106.7 (C20); 153.24 (C16).

EXAMPLE 33

Benzenesulphonic acid, 4′-methyl-[17-Allyl-1,14-dihydroxy-12-[2-(4-hydroxy-3-methoxycyclohexyl-1-methylvinyl]-23,25-dimethoxy-13,19,21,27-tetramethyl-11,28-dioxa-4-azatricyclo[22.3.1.0$^{4,9}$]octacos-18-ene-2,3,10-trione-16-ylidene]-hydrazide To a stirred solution of macrolide 900506 (23 mg) in ethanol (3 ml) was added toluene-4-sulphonylhydrazide (5.33 mg) and toluene-4-sulphonic acid (5.45 mg). The reaction mixture was stirred overnight at room temperature. Solvents were evaporated in vacuo and the residue was purified by column chromatography on silica, eluting with diethyl ether, to yield the title compound (5 mg) as an oil.

MS: (FAB) 954 (MI−OH), 972 (MI+H), 994 (MI+Na)

EXAMPLE 34

A selection of compounds were tested according to Example B. The concentration of compound required to inhibit the proliferation of lymphocytes by 50% was measured, and the results were as follows:

| Example No. of product compound | IC$_{50}$ (M) |
| --- | --- |
| 1 | <1 × 10$^{-6}$ |
| 2 | <1 × 10$^{-6}$ |
| 5 | <1 × 10$^{-6}$ |
| 6 | <1 × 10$^{-6}$ |
| 12 | <1 × 10$^{-6}$ |
| 15 | <1 × 10$^{-6}$ |
| 17 | <1 × 10$^{-6}$ |
| 18 | <1 × 10$^{-6}$ |
| 22 | <1 × 10$^{-6}$ |
| 25 | <1 × 10$^{-6}$ |
| 27 | <1 × 10$^{-6}$ |
| 30 | <1 × 10$^{-6}$ |
| 32 | <1 × 10$^{-6}$ |

We claim:

1. A compound of formula I,

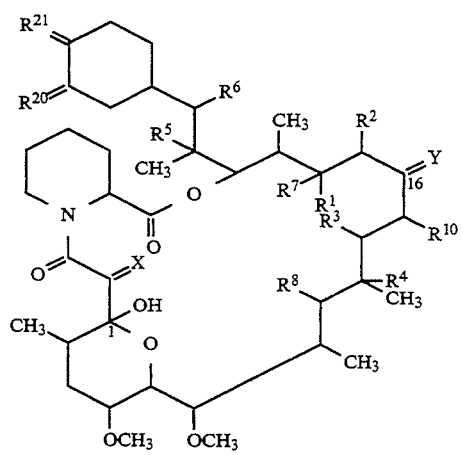

wherein each vicinal pair of substituents (R$^1$ and R$^2$), (R$^3$ and R$^4$) and (R$^5$ and R$^6$) independently:
  (a) represent two vicinal hydrogen atoms, or
  (b) form a second bond between the vicinal carbon atoms to which they are attached;
R$^7$ represents H, OH or O-alkyl;

$R^8$ represents H or OH;

$R^{10}$ represents alkyl, alkyl substituted by one or more hydroxy groups, alkenyl, alkenyl substituted by one or more hydroxy groups, or alkyl substituted by =O;

X represents O, (H, OH) or —$CH_2O$—;

Y represents O, (H, OH), N—$NR^{11}R^{12}$ or N—$OR^{13}$;

$R^{11}$ and $R^{12}$ independently represent H, alkyl, or tosyl;

$R^{13}$ represents H or alkyl;

$R^{20}$ and $R^{21}$ independently represent O, or they may independently represent ($R^{20}$a,H) and ($R^{21}$a,H), respectively; $R^{20}$a and $R^{21}$a independently represent OH, O—alkyl or $OCH_2OCH_2C$—$H_2OCH_3$; in addition $R^{20}$a and $R^{21}$a may together represent an oxygen atom in an epoxide ring;

in addition to their significances above, Y and $R^{10}$, together with the carbon atoms to which they are attached, may represent a pyrrole, di- or tetrahydrofuran ring in which the hetero atom is bonded to $C_{16}$ and which may be substituted by one or more groups selected from alkyl, hydroxy, alkyl substituted by one or more hydroxy groups, O—alkyl, benzyl and —$CH_2Se(C_6H_5)$;

provided that when X and Y both represent O; $R^{20}$a represents $OCH_3$; $R^{21}$a represents OH; ($R^2$ and $R^4$) and ($R^5$ and $R^6$) each represent a carbon-carbon atom; and (a) $R^7$ represents OH, and ($R^1$ and $R^2$) represents two vicinal hydrogen atoms, then $R^{10}$ does not represent methyl, ethyl, propyl or allyl; and (b) $R^7$ represents H and ($R^1$ and $R^2$) represents a carbon-carbon bond, then $R^{10}$ does not represent an allyl group;

and pharmaceutically acceptable salts thereof.

2. A compound according to claim 1, wherein $R^{10}$ represents allyl, propyl, ethyl or methyl.

3. A compound according to claim 1, wherein $R^7$ represents H or OH.

4. 17-Allyl-1-hydroxy-12-[2-(3,4-dimethoxycyclohexyl)-1-methylvinyl]-14,23,25-trimethoxy-13,19,21,27-tetramethyl-11,28-dioxa-4-azatricyclo[22.3.1.0$^{4,9}$]octacos-18-ene-2,3,10,16-tetraone, 17-Allyl-1,14-dihydroxy-12-[2-(3,4-dimethoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, 1,14-Dihydroxy-12-[2-(4-hydroxy-3-methoxycyclohexyl)-1-methylvinyl]-18-[(phenylseleno)methyl]-16,26,28-trimethoxy-13,22,24,30-tetramethyl-11,17,31-trioxa-4-azatetracyclo[25.3.1.0$^{4,9}$.0$^{16,20}$]hentriacont-21-ene-2,3,10-trione, 17-Allyl-1-hydroxy-12-[2-(3,4-dimethoxycyclohexyl)-1-methylvinyl]-23,25-dimethoxy-13,19,21,27-tetramethyl-11,28-dioxa-4-azatricyclo[22.3.1.0$^{4,9}$]octacosa-14,18-diene-2,3,10,16-tetraone, 17-Allyl-1,2,14-trihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-3,10,16-trione, 17-Allyl-1,2,14,16-tetrahydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-3,10-dione, 17-Propyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacosane-2,3,10,16-tetraone, 17-Propyl-1,14-dihydroxy-12-[2-(4-hydroxy-3-methoxycyclohexyl)-1-methylethyl]-23,25-dimethoxy-13,19,21,27-tetramethyl-11,28-dioxa-4-azatricyclo[22.3.1.0$^{4,9}$]octacos-18-ene-2,3,10,16-tetraone, 17-Propyl-1,14-dihydroxy-12-[2-(4-hydroxy-3-methoxycyclohexyl)-1-methylethyl]-23,25-dimethoxy-13,19,21,27-tetramethyl-11,28-dioxa-4-azatricyclo[22.3.1.0$^{4,9}$]octacosane-2,3,10,16-tetraone, 17-Propyl-1-hydroxy-12-[2-(4-hydroxy-3-methoxycyclohexyl)-1-methylvinyl-23,25-dimethoxy-13,19,21,27-tetramethyl-11,28-dioxa-4-azatricyclo[22.3.1.0$^{4,9}$]octacosa-14,18-diene-2,3,10,16-tetraone, 17-Propyl-1-hydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, 17-Allyl-1,14,20-trihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, 17-(1-Hydroxyprop-2-enyl)-1,14,20-trihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, 17-Allyl-1,2-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-3,10,16-trione, 17-Allyl-1,16-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacosa-14,18-diene-2,3,10-trione, 17-Allyl-1-hydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, 17-Propyl-1-hydroxy-12-[2-(3-methoxy-4-oxocyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, 17-(2,3-Dihydroxypropyl)-1,14-dihydroxy-12-[2-(4-hydroxy-3-methoxycyclohexyl)-1-methylvinyl]-23,25-dimethoxy-13,19,21,27,-tetramethyl-11,28-dioxa-4-azatricyclo[22.3.1.0$^{4,9}$]octacos-18-ene-2,3,10,16-tetraone, 17-Ethanalyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16,-tetraone, 1,14-Dihydroxy-12-[2-(4-hydroxy-3-methoxycyclohexyl)-1-methylvinyl]-26,28-dimethoxy-13,22,24,30-tetramethyl-11,31-dioxa-4,17-diazatetracyclo[25.3.1.0$^{4,9}$.0$^{16,20}$]hentriaconta-16(20),18,21-triene-2,3,10-trione, 1,14-Dihydroxy-12-[2-(4-hydroxy-3-methoxycyclohexyl)-1-methylvinyl]-26,28-dimethoxy-17-(2-hydroxyethyl)-13,22,24,30-tetramethyl-11,31-dioxa-4,17-diazatetracyclo[25.3.1.0.$^{4,9}$.0$^{16,20}$]hentriaconta-16(20),18,21-triene-2,3,10-trione, 1,14-Dihydroxy-12-[2-(4-hydroxy-3-methoxycyclohexyl)-1-methylvinyl]-26,28-dimethoxy-13,22,24,30-tetramethyl-17-phenylmethyl-11,31-dioxa-4,17-diazatetracyclo[25.3.1.0$^{4,9}$.0$^{16,20}$]hentriaconta-16(20),18,21-triene-2,3,10-trione, 17-Allyl-1-hydroxy-12-[2-(3,4-epoxycyclohexyl)-1-methylvinyl]-23,25-dimethoxy-13,19,21,27-tetramethyl-11,28-dioxa-4-azatricyclo[22.3.1.0$^{4,9}$]octacosa-14,18-diene-2,3,10,16-tetraone, 17-Allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone C16 oxime, 17-Allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone C16 oxime O-methyl ether, 17-Allyl-1,14-dihydroxy-12-[2-(4-(2',5'-dioxahexyloxy)-3-methoxycyclohexyl-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, 17-Propyl-1-hydroxy-12-[2-(3,4-dihydroxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, 1,14-Dihydroxy-12-[2-(4-hydroxy-3-methoxycyclohexyl)-1-methylvinyl]-23,25-dimethoxy-13,19,21,27-tetramethyl-17-(2-oxopropyl)-11,28-dioxa-4-azatricyclo[22.3.1.0$^{4,9}$]octacos-18-ene-2,3,10,16-tetraone, 17-Allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azaspiro[tricyclo[22.3.1.0$^{4,9}$]octacos-18-ene-2,2'-oxirane]-3,10,16-trione, 17-Ethanalyl-1,2,14-trihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-3,10,16-trione, 1,14-Dihydroxy-12-[2-(4-hydroxy-3-methoxycyclohexyl)-1-methylvinyl]-26,28-dimethoxy-18-[(phenylseleno)methyl]-13,22,24,30-tetramethyl-11,17,31-trioxa-4-azatetracyclo[25.3.1.0$^{4,9}$0.$^{16,20}$]hentriaconta-16(20),21-diene-2,3,10-trione, Benzenesulphonic acid, 4'-methyl-[17-Allyl-1,14-dihydroxy-12-[2-(4-hydroxy-3-methoxycyclohexyl-1-methylvinyl]-23,25-dimethoxy-13,19,21,27-tetramethyl-11,28-dioxa-4-azatricyclo[22.3.1.0$^{4,9}$]octacos-18-ene-2,3,10-trione-16-ylidene]hydrazide, or a pharmaceutically acceptable salt of any one thereof.

5. A compound according to claim 1, wherein at least one of $R^{20}a$ and $R^{21}a$ represent OH or OCH$_3$.

6. A compound according to claim 1, wherein $R^7$ represents H or OH.

7. A method of effecting immunosuppression, which comprises administering a therapeutically effective amount of a compound of formula I, as defined in claim 1, to a patient.

8. A pharmaceutical formulation comprising a compound of formula I as defined in claim 1 or a pharmaceutically acceptable salt thereof, in admixture with a pharmaceutically acceptable adjuvant, diluent or carrier.

* * * * *